United States Patent
Loy et al.

(10) Patent No.: US 10,633,517 B2
(45) Date of Patent: Apr. 28, 2020

(54) HYDROGENATED TETRAZINE-BASED ANTIOXIDANTS AND FREE RADICAL REACTION INHIBITORS AND USES THEREOF

(71) Applicant: ARIZONA BOARD OF REGENTS ON BEHALF OF THE UNIVERSITY OF ARIZONA, Tucson, AZ (US)

(72) Inventors: Douglas A. Loy, Tucson, AZ (US); Robb E. Bagge, Tucson, AZ (US); Wenmo Sun, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/917,236

(22) Filed: Mar. 9, 2018

(65) Prior Publication Data
US 2018/0258256 A1 Sep. 13, 2018

Related U.S. Application Data

(60) Provisional application No. 62/469,927, filed on Mar. 10, 2017.

(51) Int. Cl.
 *C08K 5/3477* (2006.01)
 *C07D 257/08* (2006.01)
 (Continued)

(52) U.S. Cl.
 CPC ......... *C08K 5/3477* (2013.01); *C07C 7/00* (2013.01); *C07D 231/10* (2013.01);
 (Continued)

(58) Field of Classification Search
 USPC .................. 252/405; 524/100; 544/179
 See application file for complete search history.

(56) References Cited

U.S. PATENT DOCUMENTS 2,817,662 A * 12/1957 Carboni ............... C07D 257/08
                                                           106/31.32
3,022,305 A    1/1965 Carboni
                  (Continued)

FOREIGN PATENT DOCUMENTS

WO    WO2004047568 A1    6/2004
WO    WO2009134227 A1    11/2009
                  (Continued)

OTHER PUBLICATIONS

C. D. Evans, et al, "Structure of Unsaturated Vegetable Oil Glycerides: Direct Calculation From Fatty Acid Composition," Journal of the American Oil Chemists' Society, vol. 46, 421-424 (Aug. 1969). (Year: 1969).*
(Continued)

*Primary Examiner* — Fred M Teskin
(74) *Attorney, Agent, or Firm* — Nguyen Tarbet

(57) ABSTRACT

Hydrotetrazine compounds having antioxidant properties and uses thereof are described herein. These compounds may be dihydrotetrazines, tetrahydrotetrazines, or hexahydrotetrazines that can be utilized as antioxidants for use in thermoplastics, thermosets and elastomers; free radical inhibitors to stabilize reactive chemicals, such as monomers against free radical polymerizations; and as anticorrosion agents in coatings to protect against metal oxidation. The hydrogenated tetrazines can donate hydrogen atom equivalents to terminate radical chain reactions. These compounds can change colors to signal when oxidation has occurred, and can be further recycled by reduction reactions.

18 Claims, 4 Drawing Sheets

(51) Int. Cl.

| | |
|---|---|
| *C07D 231/10* | (2006.01) |
| *C08L 25/06* | (2006.01) |
| *C08L 23/12* | (2006.01) |
| *C08L 57/00* | (2006.01) |
| *C08L 23/06* | (2006.01) |
| *C07C 7/00* | (2006.01) |
| *C09D 5/08* | (2006.01) |
| *C07C 7/20* | (2006.01) |
| *C09D 7/48* | (2018.01) |
| *C08K 5/00* | (2006.01) |

(52) U.S. Cl.
CPC ............ *C07D 257/08* (2013.01); *C08L 23/06* (2013.01); *C08L 23/12* (2013.01); *C08L 25/06* (2013.01); *C08L 57/00* (2013.01); *C09D 5/086* (2013.01); *C09D 7/48* (2018.01); *C08J 2300/22* (2013.01); *C08J 2300/24* (2013.01); *C08J 2300/26* (2013.01); *C08K 5/005* (2013.01); *C08L 2201/08* (2013.01)

(56) References Cited

U.S. PATENT DOCUMENTS

| | | | | |
|---|---|---|---|---|
| 4,389,327 A | * | 6/1983 | Rothgery | C09K 15/30 210/750 |
| 4,559,369 A | | 12/1985 | Bauman | |
| 4,704,408 A | | 11/1987 | Krug | |
| 4,847,145 A | * | 7/1989 | Matsui | B65D 81/267 428/323 |
| 5,034,463 A | | 7/1991 | Brokken-Zijp et al. | |
| 6,534,611 B1 | | 3/2003 | Darling et al. | |
| 6,866,045 B1 | | 3/2005 | Maillard et al. | |
| 2004/0262217 A1 | | 12/2004 | Mori et al. | |
| 2004/0266940 A1 | | 12/2004 | Issari | |
| 2009/0253015 A1 | | 10/2009 | Onodera et al. | |
| 2009/0264544 A1 | | 10/2009 | Loy | |
| 2010/0016545 A1 | | 1/2010 | Wiessler et al. | |
| 2011/0171076 A1 | | 7/2011 | Fansler et al. | |
| 2013/0253120 A1 | | 9/2013 | Kulkarni et al. | |
| 2013/0261272 A1 | | 10/2013 | Herzog et al. | |
| 2014/0113844 A1 | | 4/2014 | Haque et al. | |
| 2014/0371396 A1 | | 12/2014 | Van Rheenen et al. | |

FOREIGN PATENT DOCUMENTS

| | | |
|---|---|---|
| WO | WO2015121336 A1 | 8/2015 |
| WO | WO2015154078 A1 | 10/2015 |

OTHER PUBLICATIONS

Alge et al. Synthetically Tractable Click Hydrogels for Three-Dimensional Cell Culture Formed Using Tetrazine-Norbornene Chemistry. Biomacromolecules. 2013, 14, 949-953.
Desai et al. Versatile click alginate hydrogels crosslinked via tetrazineenorbornene chemistry. Biomaterials 50 (2015) 30-37.
Sukwon Jung and Hyunmin Yi. An Integrated Approach for Enhanced Protein Conjugation and Capture with Viral Nanotemplates and Hydrogel Microparticle Platforms via Rapid Bioorthogonal Reactions. Langmuir. 2014, 30, 7762-7770.
Kawamoto et al. Dual Role for 1,2,4,5-Tetrazines in Polymer Networks: Combining Diels-Alder Reactions and Metal Coordination to Generate Functional Supramolecular Gels. ACS Macro Lett. 2015, 4, 458-461.
Knall et al. Inverse electron demand Diels-Alder (iEDDA) functionalisation of macroporous poly(dicyclopentadiene) foams. Chem. Commun., 2013, 49, 7325.
Liu et al. Theoretical Elucidation of the Origins of Substituent and Strain Effects on the Rates of Diels-Alder Reactions of 1,2,4,5-Tetrazines. J. Am. Chem. Soc. 2014, 136, 11483-11493.
Liu et al. Modular and orthogonal synthesis of hybrid polymers and networks. Chem. Commun., 2015, 51, 5218.
Tork et al. Molecular Dynamics of the Diels-Alder Reactions of Tetrazines with Alkenes and N2 Extrusions from Adducts. J. Am. Chem. Soc. 2015, 137, 4749-4758.
Zhang et al. Interfacial Bioorthogonal Cross-Linking. ACS Macro Lett. 2014, 3, 727-731.
Vazquez et al. Mechanism-Based Fluorogenic trans-Cyclooctene-Tetrazine Cycloaddition. Angew. Chem. Int. Ed. 2017, 56, 1334-1337.
Heldmann et al. Synthesis of Metallated (Metal = Si, Ge, Sn) Pyridazines by Cycloaddition of Metal Substituted Alkynes to 1,2,4,5-Tetrazine. Tetrahedron Letters, vol. 38, No. 33, pp. 5791-5794, 1997.
Sauer et al. 1,2,4,5-Tetrazine: Synthesis and Reactivity in [4+2] Cycloadditions. Eur. J. Org. Chem. 1998, 2885-2896.
Kang, JW et al. Low-Loss Fluorinated Poly(Arylene Ether Sulfide) Waveguides with High 12.33Thermal Stability. Journal of Lightwave Technology. vol. 19. No. 6. Jun. 2001, pp. 872-875.
Loy D.A., Tetrazines for hydrogen storage. 59-th Annual Report on Research 2014 [online]. 55-57 Report 50941-ND7. 2014 (2014) [retrieved on Aug. 30, 2017). retrieved from the Internet: <https:llacswebcontent.acs.org/prfar/2014/Paper13084.html>. pp. 1-5.
International Search Report Issued for PCT Application No. PCT/US16/46199 dated Jan. 26, 2017.
International Search Report Issued for PCT Application No. PCT/US17/24702 dated Jun. 27, 2017.
International Search Report Issued for PCT Application No. PCT/US17/25110 dated Jun. 22, 2017.
International Search Report Issued for PCT Application No. PCT/US17/40098 dated Sep. 29, 2017.
Al-Malaika, S. In Reactive antioxidants for polymers, 1997; Blackie: 1997; pp. 266-302.
Heim, K. C. Natural polyphenol and flavonoid polymers. In: Cirillo G, Iemma F, eds. Antioxidant Polymers: Synthesis, Properties and Applications. Hoboken, NJ: Scrivener Publishing LLC and John Wiley & Sons Ltd; 2012, pp. 23-54.
Lei, H.; Huang, G.; Weng, G., Synthesis of a New Nanosilica-Based Antioxidant and Its Influence on the Anti-Oxidation Performance of Natural Rubber J. Macromol. Sci., Part B: Phys. 2013, 52, (1), 84-94.
Solera, P., New trends in polymer stabilization. J. Vinyl Addit. Technol. 1998, 4, (3), 197-210.
Cerna, A.; Cibulkova, Z.; Simon, P.; Uhlar, J.; Lehocky, P., DSC study of selected antioxidants and their binary mixtures in styrene-butadiene rubber. Polym. Degrad. Stab. 2012, 97, (9), 1724-1729.
Jaiswal, S.; Varma, P. C. R.; O'Neill, L.; Duffy, B.; Mchale, P., An investigation of the biochemical properties of tetrazines as potential coating additives. Mat Sci Eng C-Mater 2013, 33, (4), 1925-1934.
Polezhaev, A. V.; Maciulis, N. A.; Chen, C.-H.; Pink, M.; Lord, R. L.; Caulton, K. G., Tetrazine Assists Reduction of Water by Phosphines: Application in the Mitsunobu Reaction. Chem.—Eur. J. 2016, 22, (39), 13985-13998.
Audebert, P.; Sadki, S.; Miomandre, F.; Clavier, G., First example of an electroactive polymer issued from an oligothiophene substituted tetrazine. Electrochem Commun 2004, 6, (2), 144-147.
Fukuzumi, S.; Yuasa, J.; Suenobu, T., Scandium Ion-Promoted Reduction of Heterocyclic N:N Double Bond. Hydride Transfer vs Electron Transfer. J. Am. Chem. Soc. 2002, 124, (42), 12566-12573.
Knall, Chem. Commun., 2013, 49, p. 7325-7327 (Year: 2013).

\* cited by examiner

HYDROGENATED TETRAZINE-BASED ANTIOXIDANTS AND FREE RADICAL REACTION INHIBITORS AND USES THEREOF

CROSS REFERENCE

This application claims priority to U.S. Patent Application No. 62/469,927, filed Mar. 10, 2017, the specifications of which are incorporated herein in their entirety by reference.

FIELD OF THE INVENTION

The present invention relates to compounds that may be used as antioxidants and inhibitors of free radical reactions, namely, compounds that are based on hydrogenated tetrazines.

BACKGROUND OF THE INVENTION

Numerous chemical compounds that are used in industrial applications are prone to oxidative degradation. For example, certain conditions may induce the formation of free radicals in polymers, lubricants, coatings, and the like, which can be detrimental to product quality. Food products and cosmetics that contain oils and lipids may become rancid from oxidation, which can adversely affect the taste and odor of the product. In the metal industry, protective coatings may be used on metals, such as ferrous metals, to prevent corrosion. Hence, manufacturers typically add anti-oxidizing agents and free radical inhibitors to preserve their products.

However, current preservatives may possess undesirable properties that can lead to other problems. For instance, butylated hydroxyanisole (BHA) and butylated hydroxy-toluene (BHT) are common food preservatives that being scrutinized as endocrine disruptors and carcinogens. As another example, the addition of polymerization inhibitors can prolong the shelf-life of the polymer precursors; but may require an additional process to remove the inhibitors in order to maintain polymer purity. The preservatives can also become exhausted and over time, lose their effectiveness and stability. Hence, novel antioxidant compounds and inhibitors are needed as an alternatively to existing technologies.

This present invention utilizes hydrogenated tetrazines, such as dihydrotetrazines, tetrahydrotetrazines, and hexahydrotetrazines, as antioxidants or free radical reaction inhibitors. Although there exist many antioxidants based on aromatic molecules modified with hydroxyl groups (phenols), amines (aryl amines), or phosphites, there have been no reports on hydrogenated tetrazines being used as antioxidants.

Jaiswal et al. teaches the use of tetrazines as potential coating additives (Jaiswal, S.; Varma, P. C. R.; O'Neill, L.; Duffy, B.; McHale, P., An investigation of the biochemical properties of tetrazines as potential coating additives. *Mat Sci Eng C-Mater* 2013, 33, (4), 1925-1934). However, said tetrazines are amine-modified tetrazines without the hydrogen atoms, and are essentially an extension of aryl amine antioxidants that rely on single electron transfer chemistry and resonance stabilization of the resulting radical cation for antioxidant stability.

Wang et al. teaches the use of 1,4-dihydropyridine as an antioxidant (Wang, L. F.; Zhang, H. Y.; Kong, L.; Chen, Z. W.; Shi, J. G., DPT calculations indicate that 1,4-dihydropyridine is a promising lead antioxidant. *Helv Chim Acta* 2004, 87, (6), 1515-1521). However, the 1,4-dihydropyridine compound contains only one nitrogen in the ring and said nitrogen is more difficult to recycle than those in the tetrazines.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide for methods of inhibiting oxidative degradation, as specified in the independent claims. Embodiments of the invention are given in the dependent claims. Embodiments of the present invention can be freely combined with each other if they are not mutually exclusive.

In preferred embodiments, the present invention provides methods for inhibiting the oxidation of various oxidizable materials including small molecules, polymers, metals, foods, and other oxidizable materials. In other preferred embodiments, the present invention provides methods for the preparation of compositions having antioxidant properties. These methods comprise the addition of hydrogenated tetrazines to various base substrates or oxidizable materials and the resulting compositions may be used for pharmaceutical, cosmetic, packaging, coating, or other purposes.

In still further preferred embodiments, the present invention utilizes hydrogenated tetrazines as antioxidants for use in thermoplastics, thermosets and elastomers; free radical inhibitors to stabilize reactive chemicals, such as monomers against free radical polymerizations; and as anticorrosion agents in coatings to protect against metal oxidation.

One of the unique and inventive technical features of the present invention is the use of hydrogenated tetrazines, such as dihydrotetrazines, tetrahydrotetrazines, and hexahydrotetrazines, as antioxidants or free radical reaction inhibitors. Without wishing to limit the present invention to a particular theory or mechanism, the hydrotetrazines can donate two or more equivalents of hydrogen atoms to terminate radical chain reactions or oxidation reactions. The hydrotetrazines can be prepared in the synthesis of tetrazines or by hydrogenation or reduction reactions. The hydrotetrazines were found to be superior to dihydropyridazines or hindered phenols in inhibiting free radical polymerizations. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Figure 1:
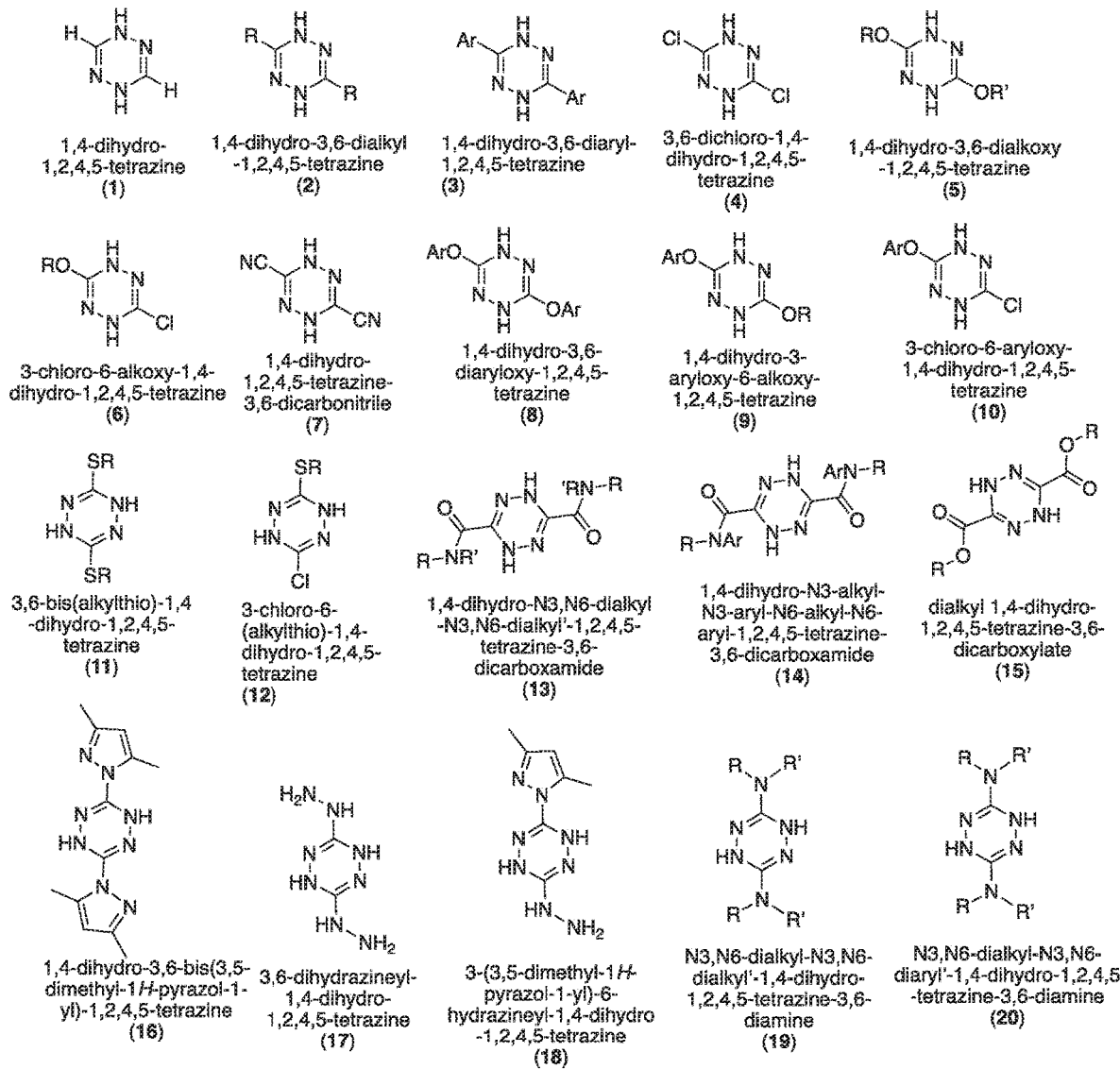
FIG. 1 illustrates non-limiting examples of dihydrotetrazines shown as only the 1,4-dihydro-1,2,4,5-tetrazine isomers. The "R" can be any alkyl moiety, including, but not limited to, methyl, ethyl, propyl, isopropyl, n-butyl, isobutyl, t-butyl, n-pentyl, isopentyl, sec-pentyl, n-hexyl, isohexyl, sec-hexyl, heptyl, octyl, octadecyl, cyclopentyl, and cyclohexyl. The "Ar" refers to any aromatic, including, but not limited to, phenyl, pyridyl, toluyl, biphenyl, naphthyl, pyrrolyl, thiophenyl, and furanyl. The "R'" can be H, an alkyl, or an aryl.

As used herein, the term "hydrotetrazine" or alternatively, "hydrogenated tetrazine", can individually, or collectively refer to, dihydrotetrazine, tetrahydrotetrazine, and hexahydrotetrazine. A hydrotetrazine compound is capable of donating 2-6 hydrogen atom equivalents to terminate radical chain reactions.

As known to one of ordinary skill in the art, the term "oxidizable" refers to a material, compound or metal which is capable of undergoing a chemical oxidation reaction with oxygen or is capable of forming additional bonds to hydrogen. Non-limiting examples of oxidizable materials include spoilable foods, unsaturated compounds, and rustable metals. Hydrotetrazines are also oxidizable and may be preferentially oxidized with respect to other oxidizable materials either because of a more kinetically or thermodynamically favored oxidation reaction or because of a superior number or position of the molecules available for oxidation.

As known to one of ordinary skill in the art, a "radical" is a species having a single, unpaired electron. A radical species that is electrically neutral may be referred to as a "free radical". An "antioxidant" is a molecule that can inhibit the oxidation of other molecules. The term "inhibit" means to prevent, hinder or to slow down a chemical process. As known to one of ordinary skill in the art, the term "unsaturated" refers to a molecule having a double or triple bond, e.g. alkene functional group. Unsaturated compounds include, but are not limited to, unsaturated oils, unsaturated lipids, unsaturated fats, and unsaturated monomers or polymer precursors. In some embodiments, unsaturated monomers can polymerize via chain radical polymerization of the alkenes. This is true for polymers such as polyethylene, polypropylene, polystyrene, and other vinylic polymers.

Dihydrotetrazines (FIG. 1), tetrahydrotetrazines (FIG. 2), and hexahydrotetrazines (FIG. 3) are reduced versions of the aromatic tetrazines that exhibit hydrogen donor chemistry capable of terminating radical chain reactions, such as oxidative degradation by oxygen ozone, peroxides, hypochlorite, hypobromite, chlorine, bromine or iodine, or free radical polymerizations, and UV induced radical chain reactions. As shown in Scheme 1, a dihydrotetrazine can donate up to two equivalents of hydrogen atoms, each of which can potentially terminate a free radical chain mechanism. The driving force for the hydrogen atom donation is the establishment of aromaticity in the 1,2,4,5-tetrazine ring. In another embodiment, each equivalent of tetrahydrotetrazine can donate up to four hydrogen atom equivalents, allowing each molecule of tetrazine to terminate four radical chain reactions. In yet another embodiment, each equivalent of the hexahydrotetrazine can similarly donate up to six hydrogen atom equivalents to terminate six free radical chain reactions.

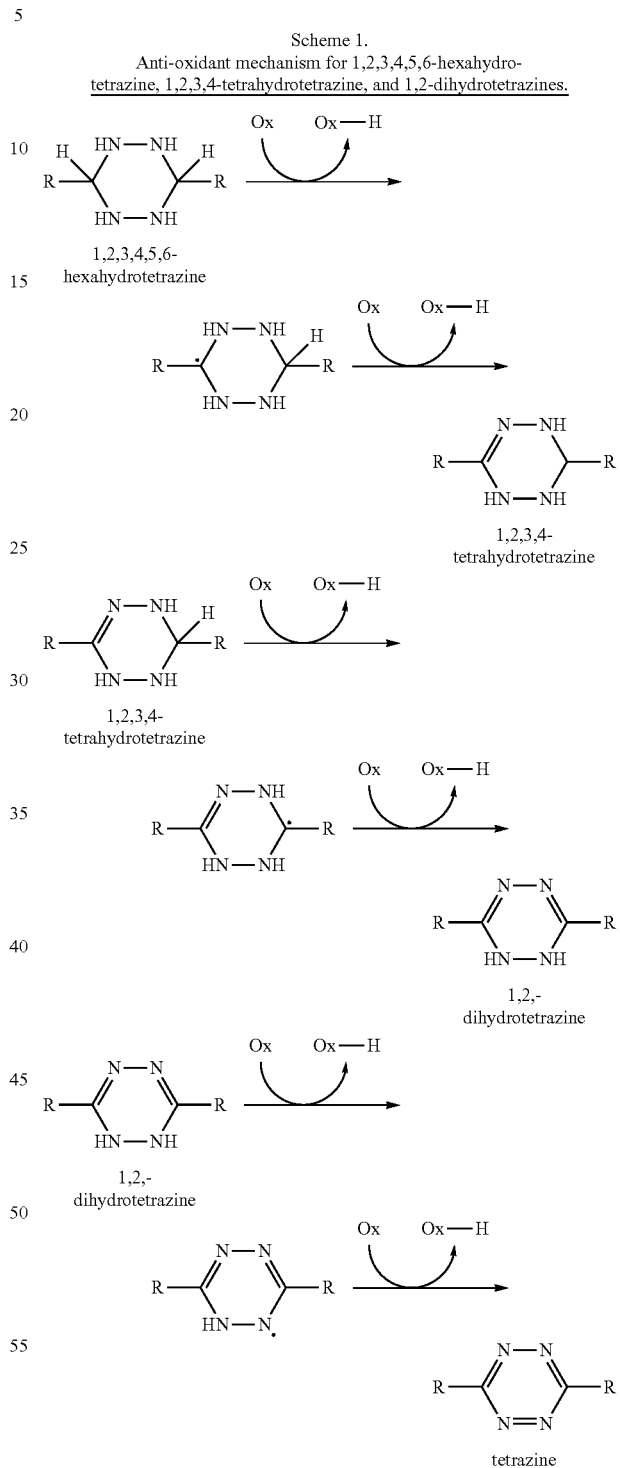

Scheme 1.
Anti-oxidant mechanism for 1,2,3,4,5,6-hexahydrotetrazine, 1,2,3,4-tetrahydrotetrazine, and 1,2-dihydrotetrazines.

Without wishing to limit the invention to a particular theory or mechanism, the dihydro-, tetrahydro- and hexahydrotetrazines possess the following characteristics that allow them to function as potent antioxidants: 1) relative abundance of hydrogen atoms that can be donated to terminate free radical chain reactions; 2) superior performance in inhibiting free radical initiated polymerizations compared with comparable amounts of antioxidants with identical hydrogen equivalency; 3) the variety of substituents on the tetrazines allowing for wide range of solubilities and use in many different polymers; 4) red-shifting of fluorescence into visible light giving rise to a visible increase in fluorescence with consumption of the tetrazine to function as self-signaling antioxidants; and 5) reduction of tetrazines after the antioxidants are exhausted allow for recycling.

Figure 2:
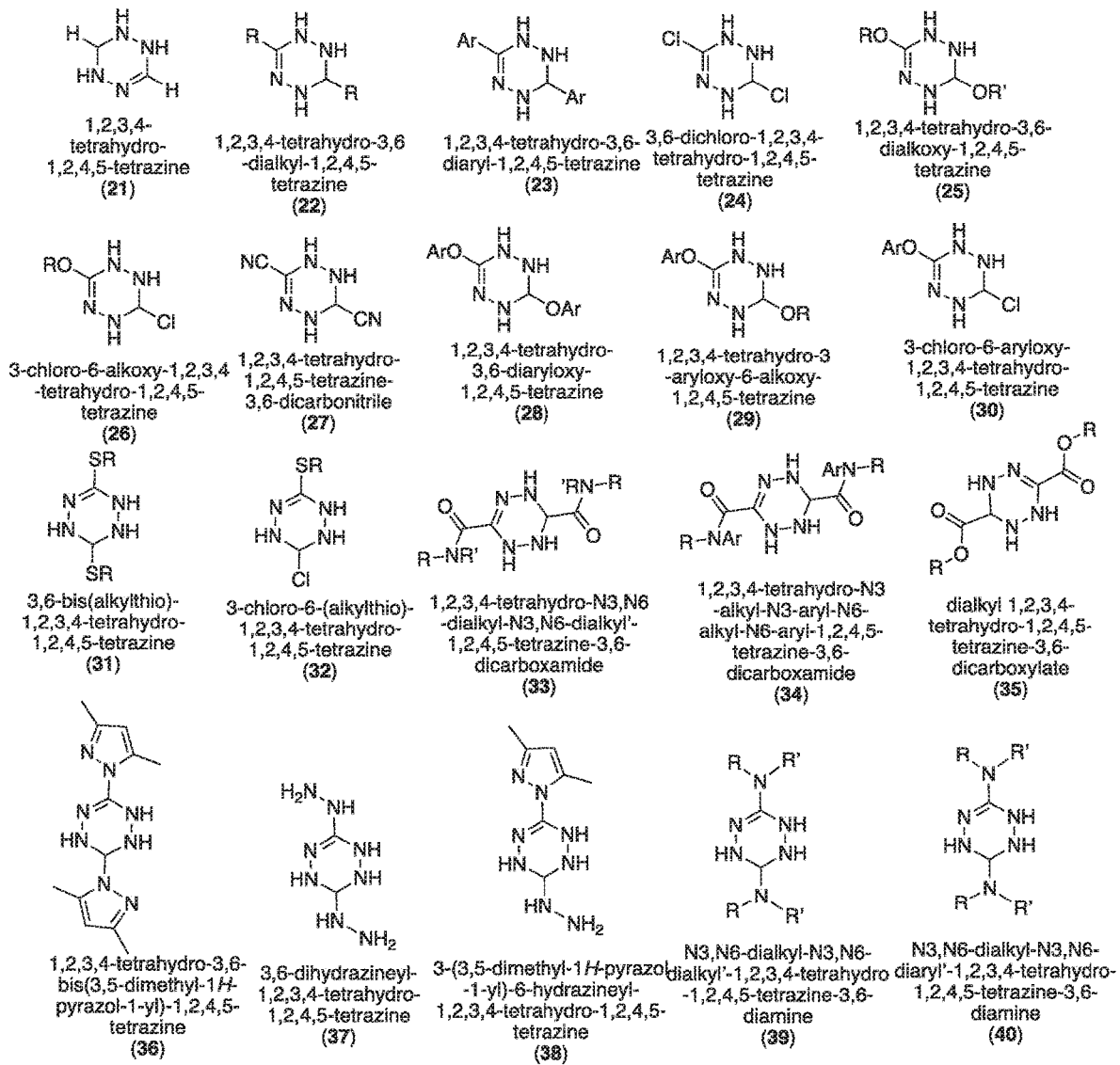
FIG. 2 illustrates non-limiting examples of tetrahydrotetrazines shown as the 1,2,3,4-tetrahydrotetrazine isomer, where R, Ar, and R' can be any of the aforementioned groups as in FIG. 1.
Figure 3:
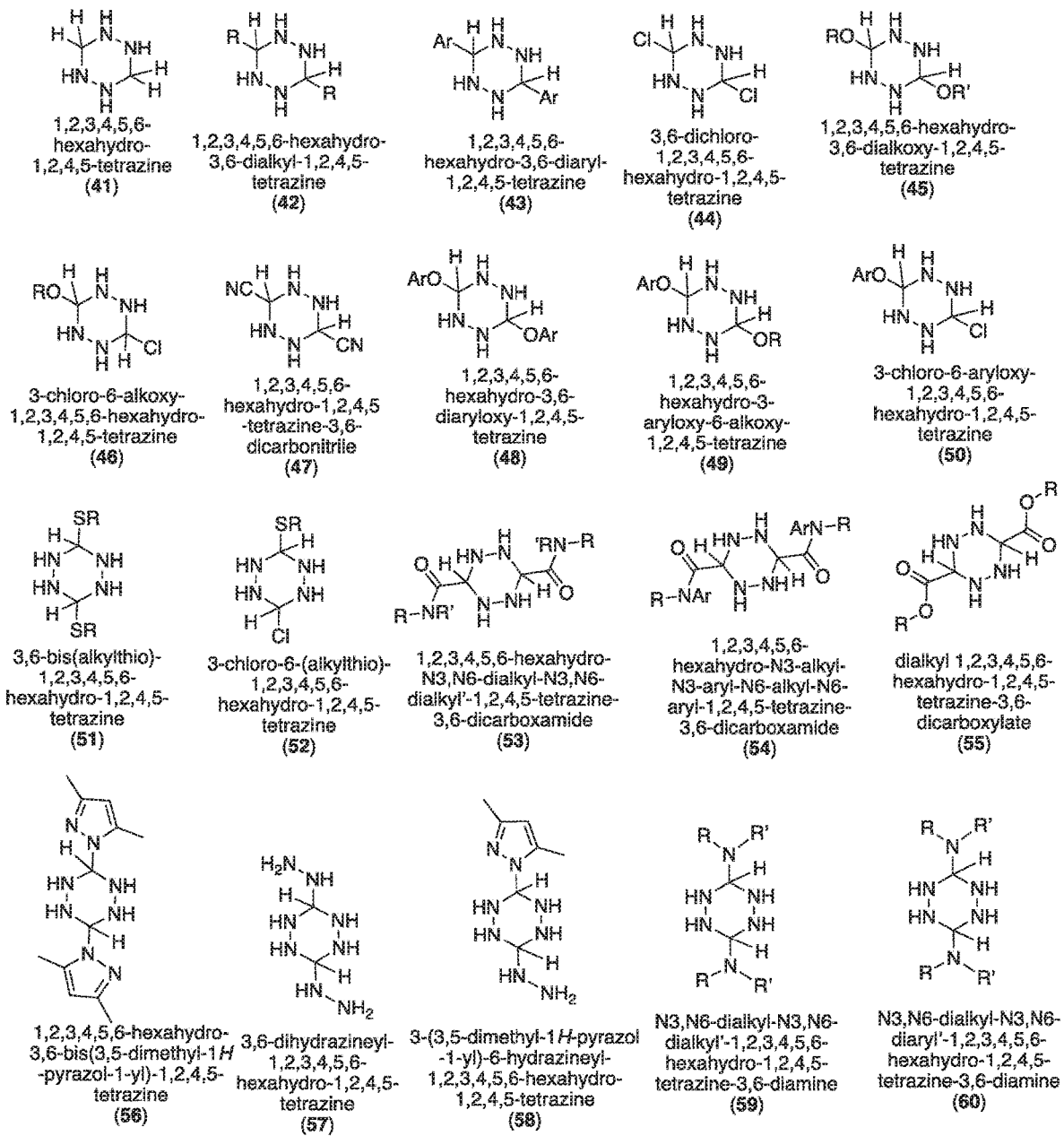
FIG. 3 shows non-limiting examples of hexahydro-1,2,3,4-tetrazine antioxidants, where R, Ar, and R' can be any of the aforementioned groups as in FIG. 1.

In some embodiments, tetrazines can be prepared with a variety of substituents at the 3 and 6 positions. Referring to FIG. 1-3, the tetrazines in this invention can include any of the disclosed substituents. In one embodiment, the R group in the dihydrotetrazines 1-20, tetrahydrotetrazines 21-40, and hexahydrotetrazines 41-60 refers to an alkyl group. Non-limiting examples of alkyls include methyl, ethyl, propyl, isopropyl, n-butyl, isobutyl, t-butyl, n-pentyl, isopentyl, sec-pentyl, n-hexyl, isohexyl, sec-hexyl, heptyl, octyl, octadecyl, cyclopentyl, and cyclohexyl. In another embodiment, the Ar may refer to an aromatic moiety such as phenyl, pyridyl, toluyl, biphenyl, naphthyl, pyrrolyl, thiophenyl, or furanyl. In yet another embodiment, the R' may refer to an H, an alkyl, or an aryl.

In one embodiment, the tetrazines may be prepared by being reduced to dihydrotetrazines by phosphines in water, by photochemical reduction, by electrochemically reduction, or by metal hydrides. For example, 1,4-Dihydro-1,2,4,5-tetrazines are frequently isolated as intermediates during the synthesis of 1,2,4,5-tetrazines. In another embodiment, dihydro-, tetrahydro- and hexahydroterazines can also be prepared by catalytic hydrogenation.

Figure 4:
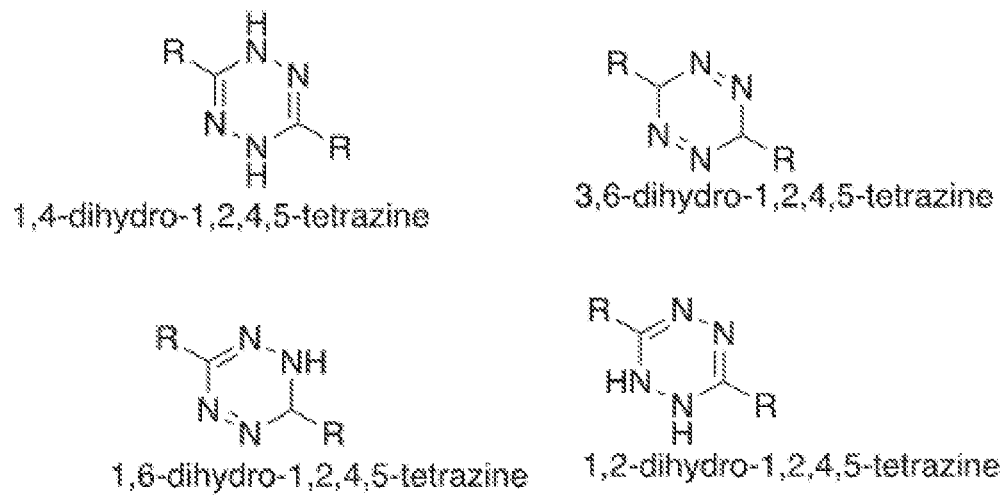
FIG. 4 shows non-limiting examples of dihydrotetrazine isomers that can be formed from catalytic hydrogenation of tetrazines, where R can be any of the aforementioned groups as in FIG. 1.
Figure 5:
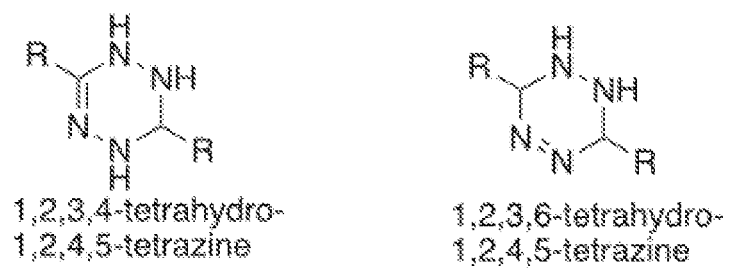
FIG. 5 shows two possible regioisomers for symmetrically substituted tetrahydrotetrazines, where R can be any of the aforementioned groups as in FIG. 1.

In some embodiments, three isomers of the dihydroterazine may also be formed. As shown in FIG. 4, these isomers are 1,2-dihydro-1,2,4,5-tetrazine, 3,6-dihydrotetazine, and 1,6-dihydro-1,2,4,5-tetrazine, which can also donate hydrogen atom equivalents. For the sake of simplicity, the dihydrotetrazines may be referred to as 1,4-dihydrotetrazines, but mean to include the other three isomers. In other embodiments, two isomers of the tetrahydrotetrazines may similarly be formed and used in accordance with the present invention.

Since it is possible to prepare the hydrogenated tetrazines by reduction reactions, it may also be possible to recycle or recharge them through chemical processing. Reduction with hydrogen in the presence of noble metals affords hydrogenated tetrazines. Again, the tetrazines can be reduced to dihydrotetrazines with phosphines in water, by photochemical reduction, by electrochemical reduction, or with metal hydrides.

According to preferred embodiments, the dihydrotetrazine, tetrahydrotetrazine, and hexahydrotetrazines compounds may be used as antioxidant additives to inhibit or retard free radical oxidation or polymerizations or oxidative corrosion through hydrogen atom donation. In one embodiment, the compounds may be used as drop in replacements for commercial antioxidants. Without wishing to limit the invention to a particular theory or mechanism, these hydrotetrazine compounds can be more effective antioxidants than comparable phenolic antioxidants, which may be due to the fact that the tetrazine product resulting from the oxidative removal of all of the hydrogen atoms can still function as an antioxidant.

In one embodiment, the present invention features a method for inhibiting oxidation of an oxidizable material. The method may comprise adding a hydrotetrazine compound to the oxidizable material, wherein when the oxidizable material and the hydrotetrazine compound are exposed to an oxidizing species, the hydrotetrazine compound is oxidized to consume the oxidizing species, thereby preventing the oxidizing species from oxidizing the oxidizable material. The oxidizable material may be a compound, a metal, an unsaturated compound, an unsaturated oil, an unsaturated lipid, an unsaturated fat, or an unsaturated monomer. In some embodiments, the oxidizable material may be coated with a film comprising the hydrotetrazine compound.

In another embodiment, the present invention features a method of preparing a composition having antioxidant properties. The method may comprise adding a hydrotetrazine compound to a base substrate to prepare the composition, wherein the hydrotetrazine compound may be oxidized to consume an oxidizing species, thereby giving the composition antioxidant properties. The composition may comprise an antioxidant packaging material, a cosmetic preparation, or a pharmaceutical preparation. The base substrate may be a small molecule, polymer, metal, powder, film, coating, or other substrate.

Referring now to FIG. 1-5, in one embodiment, the present invention features a method for inhibiting oxidation of an unsaturated compound. The method may comprise adding any one of the hydrotetrazine compounds disclosed herein to the unsaturated compound. Preferably, an amount of said hydrotetrazine compound is sufficient to inhibit oxidation of said unsaturated compound. In some embodiments, the unsaturated compound may be an unsaturated oil, an unsaturated lipid, an unsaturated fat, or an unsaturated monomer. In some embodiments, a ratio of the hydrotetrazine compound to the unsaturated compound may be 100:1, 50:1, 20:1, 10:1, 5:1, 2:1, 1:1, 1:2, 1:5, 1:10, 1:20, 1:50 or 1:100.

According to another embodiment, the present invention features a method for inhibiting corrosion of a metallic substrate. The method may comprise coating the metallic substrate with a film comprising any one of the hydrotetrazine compounds disclosed herein. For example, the metallic substrate is coated with a liquid that dries and forms a thin protective film on the metallic substrate. In a preferred embodiment, an amount of said hydrotetrazine compound is sufficient to inhibit the corrosion, such as rusting or pitting, of the metallic substrate. In some embodiments, the metallic substrate may be constructed from a ferrous material, carbon steel, stainless steel, brass, copper, alloys thereof, and the like. Examples of metallic substrates include, but are not limited to, metal sheeting, metal pipes, metal rods, metal studs, metal fasteners, metal furniture, metal containers, and metal parts for vehicles or machinery.

According to another embodiment, the present invention features a method of inhibiting free radical polymerization of unsaturated monomers. The method may comprise any one of the hydrotetrazine compounds disclosed herein to the unsaturated monomers. Preferably, an amount of said hydrotetrazine compound is sufficient to inhibit free radical polymerization of said unsaturated monomers. In one embodiment, the unsaturated monomers may comprise an alkene moiety. In another embodiment, the unsaturated monomers may be styrene monomers, ethylene monomers, propylene monomers, vinylic monomers, and the like.

In yet another embodiment, the present invention features a method of producing a packaging material. In some embodiments, the packaging material is manufactured to be in the form of a sheet, bag, box, or film. In preferred embodiments, the method may comprise applying an antioxidant to the entire surface of the packaging material. In more preferred embodiments, the antioxidant may comprise any one of the hydrotetrazine compounds disclosed herein in an amount sufficient to inhibit oxidation of a substance that is packaged in the packaging material. For example, the packaging material sheet may be used a packaging container for a food substance, such as for example, breads, cereals, grains, candy, noodles, pasta, crackers, and chips. In other embodiments, the packaging material may be used a packaging container for oils, fats, milks, and other substances that are prone to becoming rancid.

In some embodiments, the present invention features a method for stabilizing a reactive chemical composition. The method may comprise adding a hydrotetrazine compound to the reactive chemical composition, wherein the hydrotetrazine compound may be oxidized to consume a free radical species, thereby preventing the free radical species from oxidizing the reactive chemical composition or initiating free radical chain reactions of the reactive chemical composition. The hydrotetrazine compound may be added in an amount that is sufficient to inhibit oxidation and free radical chain reactions from occurring in the reactive chemical composition. In a further embodiment, the reactive chemical composition may comprise a plurality of unsaturated monomers and the prevented free radical chain reaction may be the polymerization of the unsaturated monomers. Non-limiting examples of unsaturated monomers include styrene monomers, ethylene monomers, propylene monomers, vinylic monomers, and the like.

According to other embodiments, the present invention features a method of preparing a composition having antioxidant properties. The method may comprise adding any one of the hydrotetrazine compounds disclosed herein to a base substrate. Preferably, an amount of the hydrotetrazine compound is sufficient to inhibit oxidation and free radical chain reactions. In one embodiment, the composition may be a cosmetic preparation. Examples of said cosmetic preparation include, but are not limited to, a lotion, a skin powder, a skin cream, a cleanser, a mascara, an eyeliner, a lipstick, a deodorant, a shampoo, a conditioner, a hair gel, a hair spray, a perfume, or a cologne. In another embodiment, the composition is a pharmaceutical preparation. Examples of said pharmaceutical preparation include, but are not limited to, a lozenge, a nasal spray, an oral preparation, an injectable solution, an eye preparation, a vitamin preparation, or a mineral preparation.

In yet another preferred embodiment, the hydrotetrazines can function as a self-signaling oxidation indicator. Without wishing to limit the invention to a particular theory or mechanism, the hydrotetrazines may become colored with oxidation when the replacement of hydrogen atoms with $\pi$ bonds increases the conjugation and shrinks the band gap between the highest occupied molecular orbtials (HOMO) and the lowest unoccupied molecular orbitals (LUMO). As this band gap shrinks, the electromagnetic radiation that will excite electrons to the LUMO is lower in energy. This shifts the absorption and fluorescence into the visible region. Thus, as the antioxidant is consumed, their color can shift from colorless to a red, orange, or yellow color, and their fluorescence under ultraviolet light can become visible.

In some embodiments, since the tetrahydrotetrazines have twice the number of hydrogens than the dihydrotetrazines, this allows for twice as many radical chain reactions to be intercepted. In other embodiments, the hexahydrotetrazines have three times as many hydrogen atoms as the dihydrotetrazines, thereby making them the most potent antioxidants of the hydrotetrazines. In still other embodiments, the variety of different substituents and levels of hydrogenation will provide the diversity in solubility to allow the antioxidants to be soluble in practically any commercial polymer, including polymers used for protective coatings for preventing metal corrosion.

According to some embodiments, the hydrotetrazine may be added to the polymer during the melt processing of the resin, similar to hindered phenolic compounds. Preferably, the temperature during the melt process is kept below 150° C. when using compounds 16, 17, 18, 36, 37, 38, 56, 57, and 58. These nine compounds, in particular, may decompose into nitrogen gas and nitriles with heating above 150° C.

According to other embodiments, the dihydrotetrazines, tetrahydrotetrazines, and hexahydrotetrazines may be added to vinyl monomers as free radical polymerization inhibitors to prevent the monomers from prematurely polymerizing. In the examples that follow, the capability of dihydrotetrazines in delaying the onset of free radical initiated polymerization of divinyl benzene initiated by 1 mol % azoisobutyronitrile (AIBN) is demonstrated.

EXAMPLES

The following are non-limiting examples of the present invention, in particular, the use of dihydroterazine as an antioxidant. The examples are for illustrative purposes only and are not intended to limit the invention in any way. Equivalents or substitutes are within the scope of the invention.

Blank Control:

A 20 mL glass scintillation vial was charged with divinylbenzene (1.73 g, 13.33 mmol), azobisiobutyronitrile (AIBN) (0.044 g, 0.27 mmol), and a magnetic stir bar. The vial was capped with a rubber septum and the solution purged with argon while stirring for 30 minutes. The vial was then transferred to a 70° C. oil bath and left undisturbed. After 3 minutes, an opaque white solid was observed to have formed in the vial.

Control with BHT:

A 20 mL glass scintillation vial was charged with divinylbenzene (1.73 g, 13.33 mmol), AIBN (0.044 g, 0.27 mmol), BHT (0.059 g, 0.27 mmol), and a magnetic stir bar. The vial was capped with a rubber septum and the solution purged with argon while stirring for 30 minutes. The vial was then transferred to a 70° C. oil bath and left undisturbed. After 4.5 minutes, a transparent solid was observed to have formed in the vial. And after 8.5 minutes, the transparent solid turned to opaque.

Dihydrotetrazine:

A 20 mL glass scintillation vial was charged with divinylbenzene (1.73 g, 13.33 mmol), AIBN (0.044 g, 0.27 mmol), 3,6-bis(3,5-dimethyl-1H-pyrazol-1-yl)-1,4-dihydro-1,2,4,5-tetrazine (0.073 g, 0.27 mmol), and a magnetic stir bar. The vial was capped with a rubber septum and the solution purged with argon while stirring for 30 minutes. The vial was then transferred to a 70° C. oil bath and left undisturbed. After 6 minutes, a yellow solid was observed to have formed in the vial.

Normally, the free radical polymerization of divinylbenzene rapidly leads to gels, providing a visual indication of free radical polymerization. In the aforementioned examples, the relative effectiveness of free radical inhibitors are determined by how much a standard quantity delays the onset of gelation. In the presence of 1 mol % AIBN, divinylbenzene will polymerize with crosslinking to form a gel in 3 minutes. Addition of 1 mol % BHT to divinylbenzene delays gelation by 50% to 4.5 minutes. With 1 mol % of 3,6-bis(3,5-dimethyl-1H-pyrazol-1-yl)-1,4-dihydro-1,2,4,5-tetrazine, gelation of divinyl-benzene was delayed six minutes or 100% longer than without the inhibitor and 33% longer than with an equivalent amount of BHT.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method for inhibiting oxidation of an oxidizable material, comprising adding a hydrotetrazine compound to the oxidizable material, the hydrotetrazine compound is selected from: a 1,4-dihydrotetrazine, a tetrahydrotetrazine, or a hexahydrotetrazine, wherein the hydrotetrazine compound is oxidized to consume oxidizing species exposed to the hydrotetrazine, thereby preventing the oxidizing species from oxidizing the oxidizable material.

2. The method of claim 1, wherein the oxidizable material is a compound, a metal, an unsaturated compound, an unsaturated oil, an unsaturated lipid, an unsaturated fat, or an unsaturated monomer.

3. The method of claim 1, wherein the oxidizable material is coated with a film comprising the hydrotetrazine compound.

4. The method of claim 1, wherein the hydrotetrazine compound is configured to change color when undergoing an oxidation reaction.

5. The method of claim 1, wherein the hydrotetrazine compound is configured to be regenerated by undergoing a reduction reaction, a reaction with phosphines in water, a photochemical reduction, an electrochemical reduction, or a reaction with metal hydrides.

6. The method of claim 1, wherein the 1,4-dihydrotetrazine is selected from:

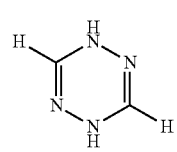

1,4-dihydro-1,2,4,5-tetrazine (1)

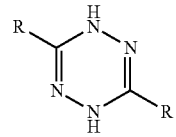

1,4-dihydro-3,6-dialkyl-1,2,4,5-tetrazine (2)

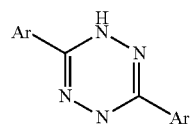

1,4-dihydro-3,6-diaryl-1,2,4,5-tetrazine (3)

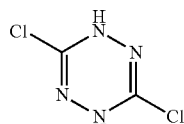

3,6-dichloro-1,4-dihydro-1,2,4,5-tetrazine (4)

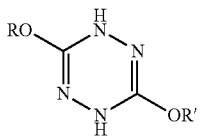

1,4-dihydro-3,6-dialkoxy-1,2,4,5-tetrazine (5)

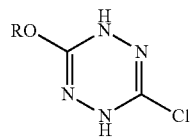

3-chloro-6-alkoxy-1,4-dihydro-1,2,4,5-tetrazine (6)

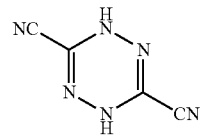

1,4-dihydro-1,2,4,5-tetrazine-3,6-dicarbonitrile (7)

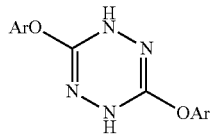

1,4-dihydro-3,6-diaryloxy-1,2,4,5-tetrazine (8)

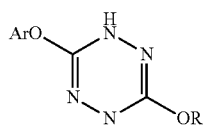

1,4-dihydro-3-aryloxy-6-alkoxy-1,2,4,5-tetrazine (9)

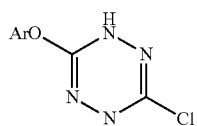

3-chloro-6-aryloxy-1,4-dihydro-1,2,4,5-tetrazine (10)

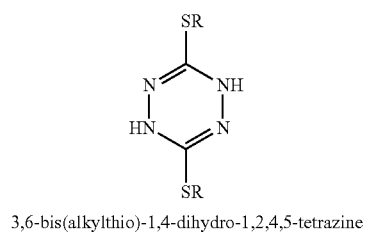

3,6-bis(alkylthio)-1,4-dihydro-1,2,4,5-tetrazine (11)

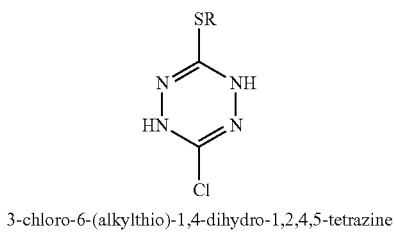

3-chloro-6-(alkylthio)-1,4-dihydro-1,2,4,5-tetrazine (12)

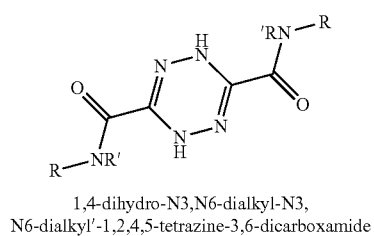

1,4-dihydro-N3,N6-dialkyl-N3,N6-dialkyl'-1,2,4,5-tetrazine-3,6-dicarboxamide (13)

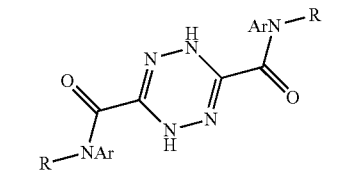

1,4-dihydro-N3-alkyl-N3-aryl-N6-alkyl-N6-aryl-1,2,4,5-tetrazine-3,6-dicarboxamide (14)

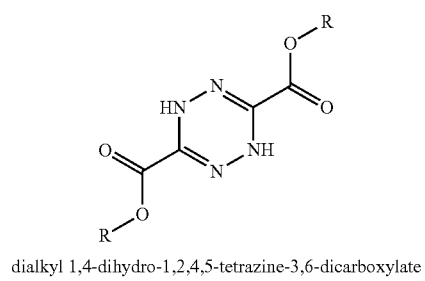

dialkyl 1,4-dihydro-1,2,4,5-tetrazine-3,6-dicarboxylate (15)

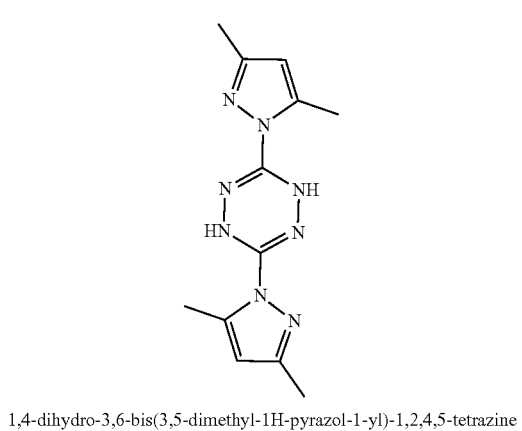

1,4-dihydro-3,6-bis(3,5-dimethyl-1H-pyrazol-1-yl)-1,2,4,5-tetrazine (16)

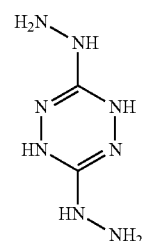

3,6-dihydrazineyl-1,4-dihydro-1,2,4,5-tetrazine (17)

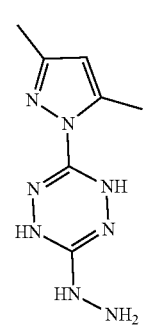

3-(3,5-dimethyl-1H-pyrazol-1-yl)-6-hydrazineyl-1,4-dihydro-1,2,4,5-tetrazine (18)

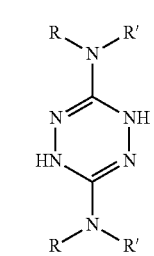

N3,N6-dialkyl-N3,N6-dialkyl'-1,4-dihydro-1,2,4,5-tetrazine-3,6-diamine (19)

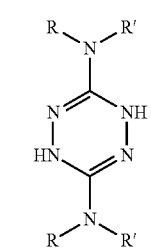

N3,N6-dialkyl-N3,N6-diaryl'-1,4-dihydro-1,2,4,5-tetrazine-3,6-diamine. (20)

7. The method of claim 1, wherein the tetrahydrotetrazine is selected from:

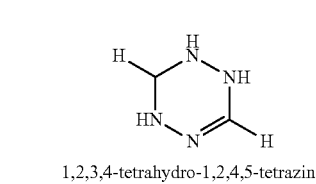

1,2,3,4-tetrahydro-1,2,4,5-tetrazine (21)

-continued

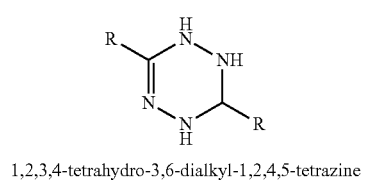

1,2,3,4-tetrahydro-3,6-dialkyl-1,2,4,5-tetrazine (22)

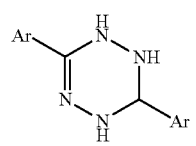

1,2,3,4-tetrahydro-3,6-diaryl-1,2,4,5-tetrazine (23)

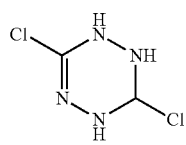

3,6-dichloro-1,2,3,4-tetrahydro-1,2,4,5-tetrazine (24)

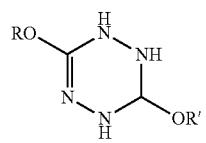

1,2,3,4-tetrahydro-3,6-dialkoxy-1,2,4,5-tetrazine (25)

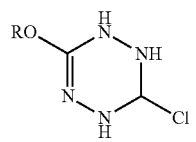

3-chloro-6-alkoxy-1,2,3,4-tetrahydro-1,2,4,5-tetrazine (26)

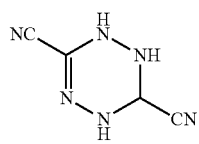

1,2,3,4-tetrahydro-1,2,4,5-tetrazine-3,6-dicarbonitrile (27)

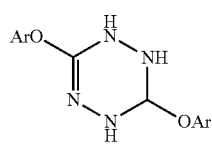

1,2,3,4-tetrahydro-3,6-diaryloxy-1,2,4,5-tetrazine (28)

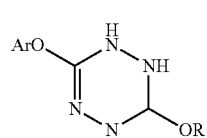

1,2,3,4-tetrahydro-3-aryloxy-6-alkoxy-1,2,4,5-tetrazine (29)

-continued

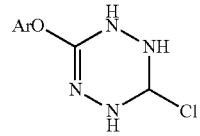

3-chloro-6-aryloxy-1,2,3,4-tetrahydro-1,2,4,5-tetrazine (30)

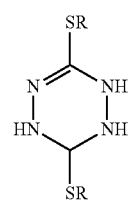

3,6-bis(alkylthio)-1,2,3,4-tetrahydro-1,2,4,5-tetrazine (31)

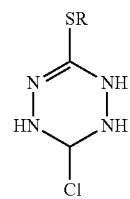

3-chloro-6-(alkylthio)-1,2,3,4-tetrahydro-1,2,4,5-tetrazine (32)

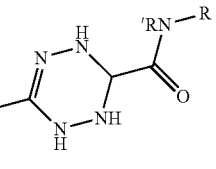

1,2,3,4-tetrahydro-N3,N6-dialkyl-N3,
N6-dialkyl'-1,2,4,5-tetrazine-3,6-dicarboxamide (33)

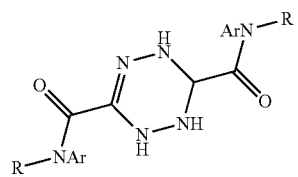

1,2,3,4-tetrahydro-N3-alkyl-N3-aryl-N6-alkyl-
N6-aryl-1,2,4,5-tetrazine-3,6-dicarboxamide (34)

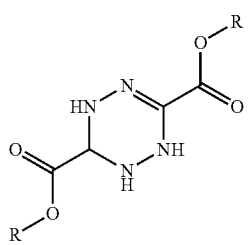

dialkyl 1,2,3,4-tetrahydro-1,2,4,5-tetrazine-3,6-dicarboxylate (35)

-continued

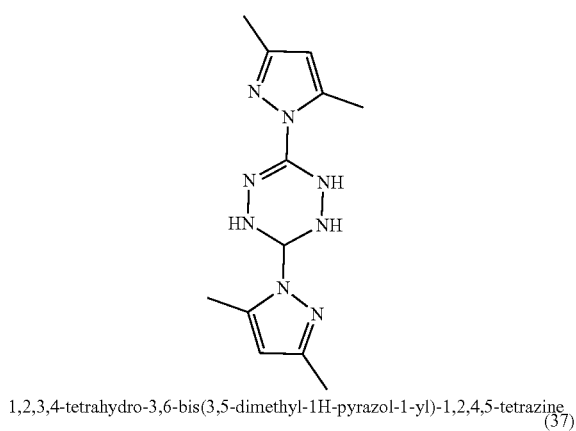

1,2,3,4-tetrahydro-3,6-bis(3,5-dimethyl-1H-pyrazol-1-yl)-1,2,4,5-tetrazine

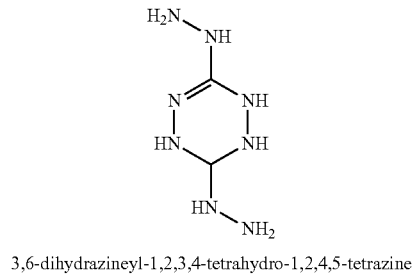

3,6-dihydrazineyl-1,2,3,4-tetrahydro-1,2,4,5-tetrazine

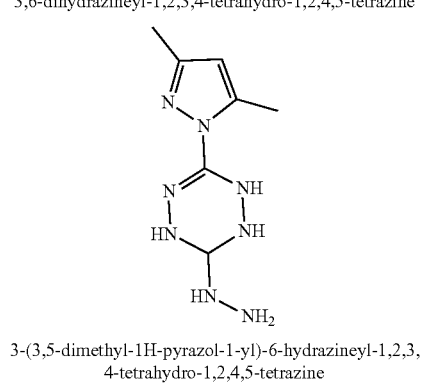

3-(3,5-dimethyl-1H-pyrazol-1-yl)-6-hydrazineyl-1,2,3,4-tetrahydro-1,2,4,5-tetrazine

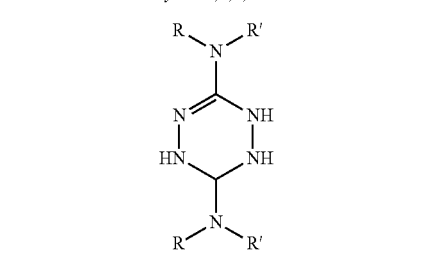

N3,N6-dialkyl-N3,N6-dialkyl'-1,2,3,4-tetrahydro-1,2,4,5-tetrazine-3,6-diamine

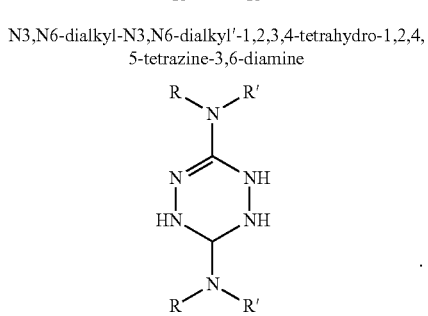

N3,N6-dialkyl-N3,N6-diaryl'-1,2,3,4-tetrahydro-1,2,4,5-tetrazine-3,6-diamine

8. The method of claim 1, wherein the hexahydrotetrazine is selected from:

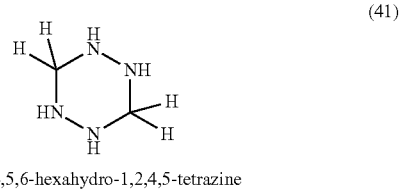

1,2,3,4,5,6-hexahydro-1,2,4,5-tetrazine

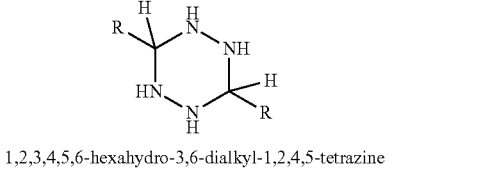

1,2,3,4,5,6-hexahydro-3,6-dialkyl-1,2,4,5-tetrazine

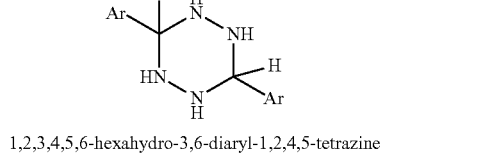

1,2,3,4,5,6-hexahydro-3,6-diaryl-1,2,4,5-tetrazine

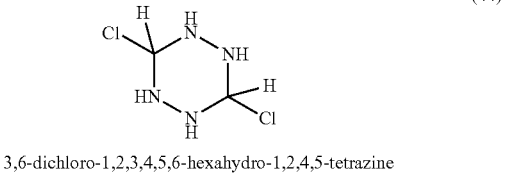

3,6-dichloro-1,2,3,4,5,6-hexahydro-1,2,4,5-tetrazine

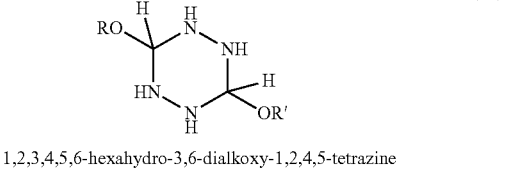

1,2,3,4,5,6-hexahydro-3,6-dialkoxy-1,2,4,5-tetrazine

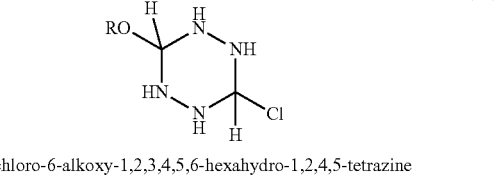

3-chloro-6-alkoxy-1,2,3,4,5,6-hexahydro-1,2,4,5-tetrazine

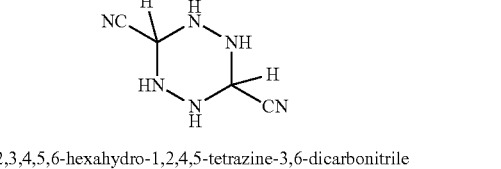

1,2,3,4,5,6-hexahydro-1,2,4,5-tetrazine-3,6-dicarbonitrile

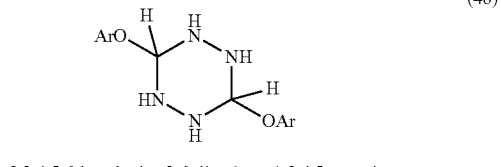

1,2,3,4,5,6-hexahydro-3,6-diaryloxy-1,2,4,5-tetrazine

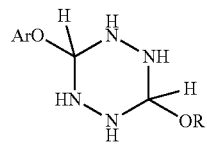

1,2,3,4,5,6-hexahydro-3-aryloxy-6-alkoxy-1,2,4,5-tetrazine (49)

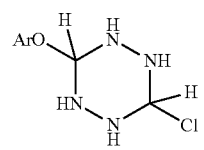

3-chloro-6-aryloxy-1,2,3,4,5,6-hexahydro-1,2,4,5-tetrazine (50)

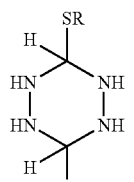

3,6-bis(alkylthio)-1,2,3,4,5,6-hexahydro-1,2,4,5-tetrazine (51)

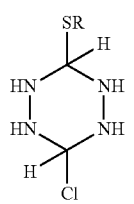

3-chloro-6-(alkylthio)-1,2,3,4,5,6-hexahydro-1,2,4,5-tetrazine (52)

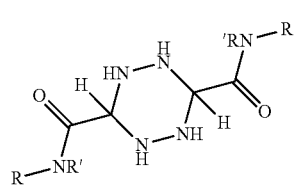

1,2,3,4,5,6-hexahydro-N3,N6-dialkyl-N3,N6-dialkyl'-1,2,4,5-tetrazine-3,6-dicarboxamide (53)

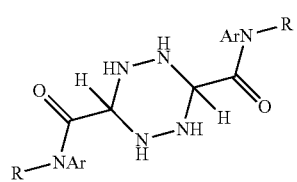

1,2,3,4,5,6-hexahydro-N3-alkyl-N3-aryl-N6-alkyl-N6-aryl-1,2,4,5-tetrazine-3,6-dicarboxamide (54)

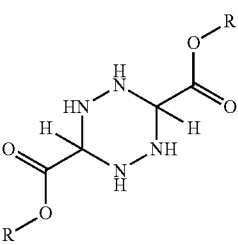

dialkyl 1,2,3,4,5,6-hexahydro-1,2,4,5-tetrazine-3,6-dicarboxylate (55)

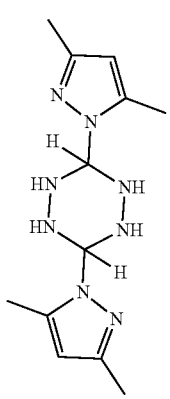

1,2,3,4,5,6-hexahydro-3,6-bis(3,5-dimethyl-1H-pyrazol-1-yl)-1,2,4,5-tetrazine (56)

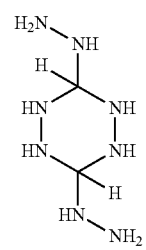

3,6-dihydrazineyl-1,2,3,4,5,6-hexahydro-1,2,4,5-tetrazine (57)

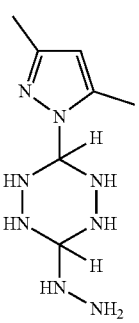

3-(3,5-dimethyl-1H-pyrazol-1-yl)-6-hydrazineyl-1,2,3,4,5,6-hexahydro-1,2,4,5-tetrazine (58)

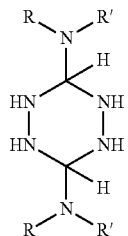

N3,N6-dialkyl-N3,N6-dialkyl'-1,2,3,4,5,6-hexahydro-1,2,4,5-tetrazine-3,6-diamine (59)

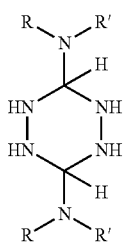

N3,N6-dialkyl-N3,N6-diaryl'-1,2,3,4,5,6-hexahydro-1,2,4,5-tetrazine-3,6-diamine (60)

9. A method for stabilizing a reactive chemical composition, comprising adding a hydrotetrazine compound to the reactive chemical composition, the hydrotetrazine compound is selected from: a 1,4-dihydrotetrazine, a tetrahydrotetrazine, or a hexahydrotetrazine, wherein the hydrotetrazine compound is oxidized to consume a free radical species, thereby preventing the free radical species from oxidizing the reactive chemical composition or initiating free radical chain reactions of the reactive chemical composition.

10. The method of claim 9, wherein the reactive chemical composition comprises a plurality of unsaturated monomers and the prevented free radical chain reaction is the polymerization of the unsaturated monomers.

11. The method of claim 10, wherein the unsaturated monomers are styrene monomers, ethylene monomers, propylene monomers, vinylic monomer.

12. The method of claim 9, wherein the hydrotetrazine compound is configured to change color when undergoing an oxidation reaction.

13. The method of claim 9, wherein the hydrotetrazine compound is configured to be regenerated by undergoing a reduction reaction, a reaction with phosphines in water, a photochemical reduction, an electrochemical reduction, or a reaction with metal hydrides.

14. The method of claim 9, wherein the 1,4-dihydrotetrazine is selected from:

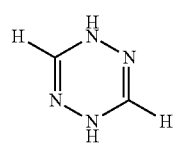

1,4-dihydro-1,2,4,5-tetrazine (1)

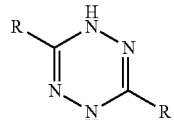

1,4-dihydro-3,6-dialkyl-1,2,4,5-tetrazine (2)

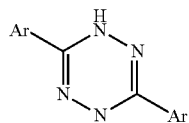

1,4-dihydro-3,6-diaryl-1,2,4,5-tetrazine (3)

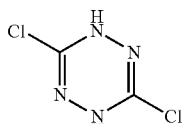

3,6-dichloro-1,4-dihydro-1,2,4,5-tetrazine (4)

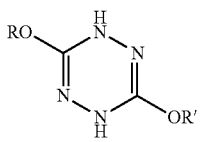

1,4-dihydro-3,6-dialkoxy-1,2,4,5-tetrazine (5)

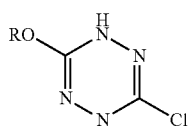

3-chloro-6-alkoxy-1,4-dihydro-1,2,4,5-tetrazine (6)

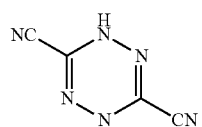

1,4-dihydro-1,2,4,5-tetrazine-3,6-dicarbonitrile (7)

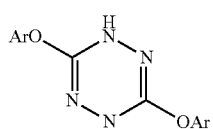

1,4-dihydro-3,6-diaryloxy-1,2,4,5-tetrazine (8)

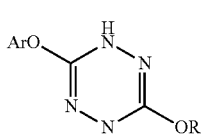

1,4-dihydro-3-aryloxy-6-alkoxy-1,2,4,5-tetrazine (9)

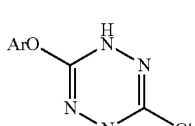

3-chloro-6-aryloxy-1,4-dihydro-1,2,4,5-tetrazine (10)

-continued

(11)
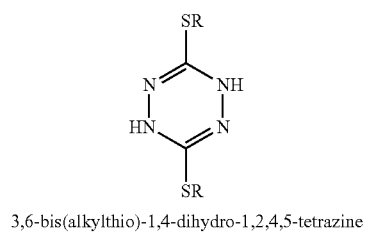
3,6-bis(alkylthio)-1,4-dihydro-1,2,4,5-tetrazine

(12)
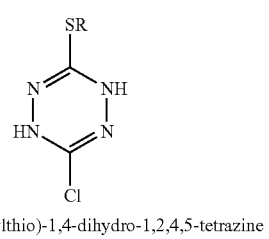
3-chloro-6-(alkylthio)-1,4-dihydro-1,2,4,5-tetrazine

(13)
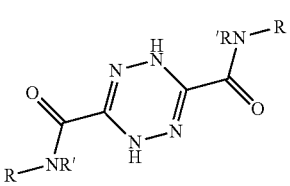
1,4-dihydro-N3,N6-dialkyl-N3,
N6-dialkyl'-1,2,4,5-tetrazine-3,6-dicarboxamide

(14)
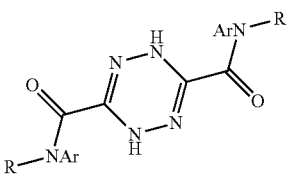
1,4-dihydro-N3-alkyl-N3-aryl-N6-alkyl-
N6-aryl-1,2,4,5-tetrazine-3,6-dicarboxamide

(15)
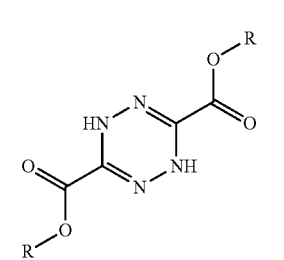
dialkyl 1,4-dihydro-1,2,4,5-tetrazine-3,6-dicarboxylate -continued

(16)
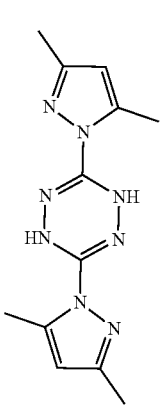
1,4-dihydro-3,6-bis(3,5-dimethyl-1H-pyrazol-1-yl)-1,2,4,5-tetrazine

(17)
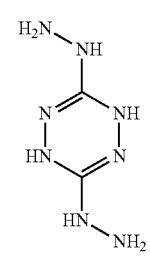
3,6-dihydrazineyl-1,4-dihydro-1,2,4,5-tetrazine

(18)
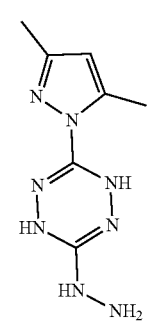
3-(3,5-dimethyl-1H-pyrazol-1-yl)-6-
hydrazineyl-1,4-dihydro-1,2,4,5-tetrazine

(19)
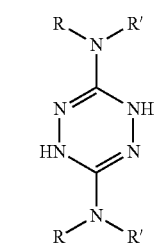
N3,N6-dialkyl-N3,N6-dialkyl'-1,4-dihydro-1,2,4,5-tetrazine-3,6-diamine

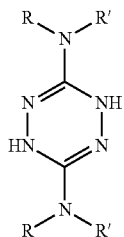

N3,N6-dialkyl-N3,N6-diaryl′-1,4-dihydro-1,2,4,5-tetrazine-3,6-diamine.

15. The method of claim 9, wherein the tetrahydrotetrazine is selected from:

(21)

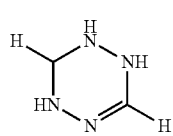

1,2,3,4-tetrahydro-1,2,4,5-tetrazine (22)

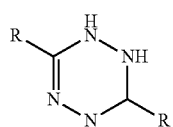

1,2,3,4-tetrahydro-3,6-dialkyl-1,2,4,5-tetrazine (23)

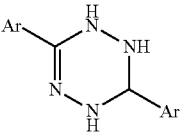

1,2,3,4-tetrahydro-3,6-diaryl-1,2,4,5-tetrazine (24)

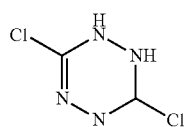

3,6-dichloro-1,2,3,4-tetrahydro-1,2,4,5-tetrazine (25)

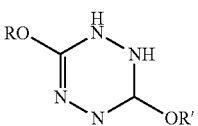

1,2,3,4-tetrahydro-3,6-dialkoxy-1,2,4,5-tetrazine (26)

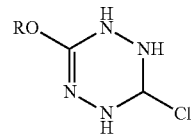

3-chloro-6-alkoxy-1,2,3,4-tetrahydro-1,2,4,5-tetrazine (27)

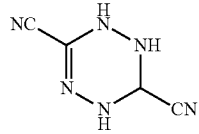

1,2,3,4-tetrahydro-1,2,4,5-tetrazine-3,6-dicarbonitrile (28)

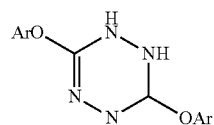

1,2,3,4-tetrahydro-3,6-diaryloxy-1,2,4,5-tetrazine (29)

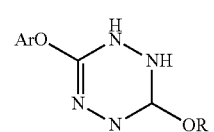

1,2,3,4-tetrahydro-3-aryloxy-6-alkoxy-1,2,4,5-tetrazine (30)

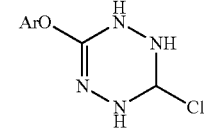

3-chloro-6-aryloxy-1,2,3,4-tetrahydro-1,2,4,5-tetrazine (31)

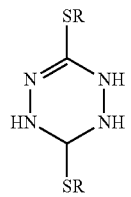

3,6-bis(alkylthio)-1,2,3,4-tetrahydro-1,2,4,5-tetrazine (32)

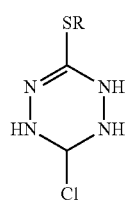

3-chloro-6-(alkylthio)-1,2,3,4-tetrahydro-1,2,4,5-tetrazine (33)

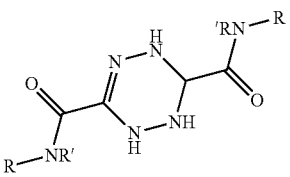

1,2,3,4-tetrahydro-N3,N6-dialkyl-N3,
N6-dialkyl′-1,2,4,5-tetrazine-3,6-dicarboxamide -continued

(34)
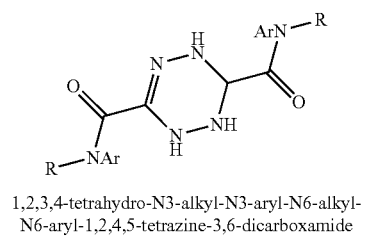
1,2,3,4-tetrahydro-N3-alkyl-N3-aryl-N6-alkyl-
N6-aryl-1,2,4,5-tetrazine-3,6-dicarboxamide

(35)
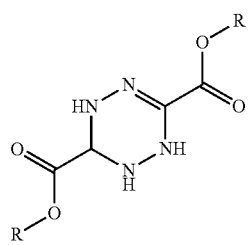
dialkyl 1,2,3,4-tetrahydro-1,2,4,5-tetrazine-3,6-dicarboxylate

(36)
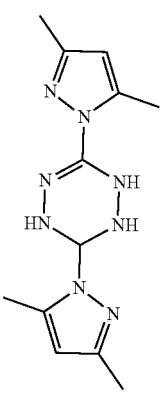
1,2,3,4-tetrahydro-3,6-bis(3,5-dimethyl-1H-pyrazol-1-yl)-1,2,4,5-tetrazine

(37)
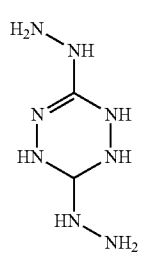
3,6-dihydrazineyl-1,2,3,4-tetrahydro-1,2,4,5-tetrazine

(38)
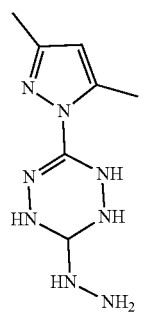
3-(3,5-dimethyl-1H-pyrazol-1-yl)-6-hydrazineyl-1,2,3,4-tetrahydro-1,2,4,5-tetrazine -continued

(39)
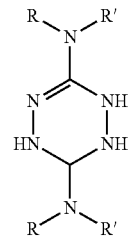
N3,N6-dialkyl-N3,N6-dialkyl'-1,2,3,4-tetrahydro-1,2,4,5-tetrazine-3,6-diamine

(40)
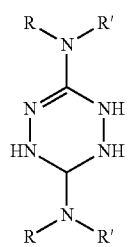
N3,N6-dialkyl-N3,N6-diaryl'-1,2,3,4-tetrahydro-1,2,4,5-tetrazine-3,6-diamine 16. The method of claim 9, wherein the hexahydrotetrazine is selected from:

(41)
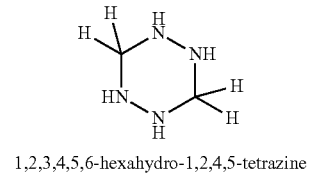
1,2,3,4,5,6-hexahydro-1,2,4,5-tetrazine

(42)
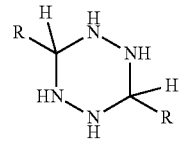
1,2,3,4,5,6-hexahydro-3,6-dialkyl-1,2,4,5-tetrazine

(43)
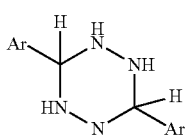
1,2,3,4,5,6-hexahydro-3,6-diaryl-1,2,4,5-tetrazine

(44)
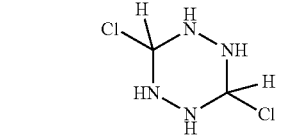
3,6-dichloro-1,2,3,4,5,6-hexahydro-1,2,4,5-tetrazine

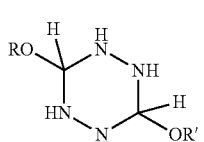

1,2,3,4,5,6-hexahydro-3,6-dialkoxy-1,2,4,5-tetrazine (45)

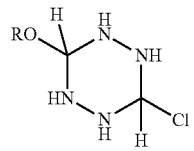

3-chloro-6-alkoxy-1,2,3,4,5,6-hexahydro-1,2,4,5-tetrazine (46)

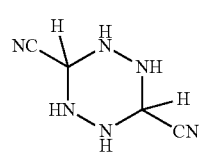

1,2,3,4,5,6-hexahydro-1,2,4,5-tetrazine-3,6-dicarbonitrile (47)

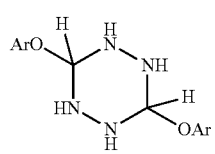

1,2,3,4,5,6-hexahydro-3,6-diaryloxy-1,2,4,5-tetrazine (48)

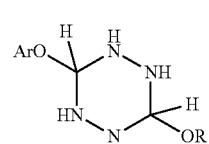

1,2,3,4,5,6-hexahydro-3-aryloxy-6-alkoxy-1,2,4,5-tetrazine (49)

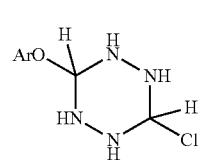

3-chloro-6-aryloxy-1,2,3,4,5,6-hexahydro-1,2,4,5-tetrazine (50)

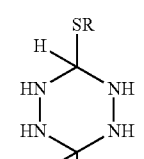

3,6-bis(alkylthio)-1,2,3,4,5,6-hexahydro-1,2,4,5-tetrazine (51)

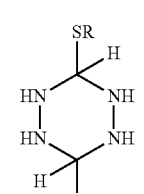

3-chloro-6-(alkylthio)-1,2,3,4,5,6-hexahydro-1,2,4,5-tetrazine (52)

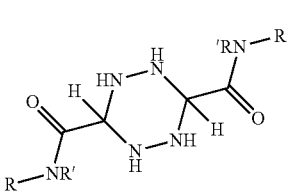

1,2,3,4,5,6-hexahydro-N3,N6-dialkyl-N3,N6-dialkyl'-1,2,4,5-tetrazine-3,6-dicarboxamide (53)

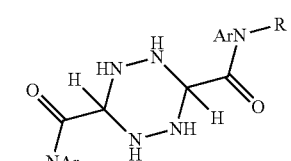

1,2,3,4,5,6-hexahydro-N3-alkyl-N3-aryl-N6-alkyl-N6-aryl-1,2,4,5-tetrazine-3,6-dicarboxamide (54)

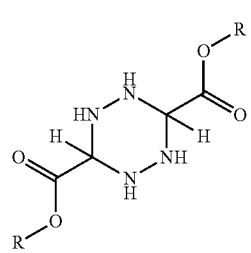

dialkyl 1,2,3,4,5,6-hexahydro-1,2,4,5-tetrazine-3,6-dicarboxylate (55)

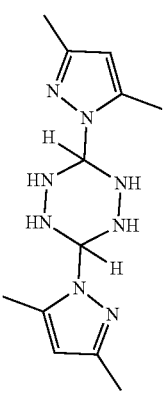

1,2,3,4,5,6-hexahydro-3,6-bis(3,5-dimethyl-1H-pyrazol-1-yl)-1,2,4,5-tetrazine (56)

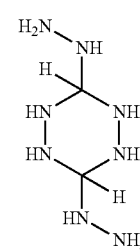

3,6-dihydrazineyl-1,2,3,4,5,6-hexahydro-1,2,4,5-tetrazine (57)

(58)

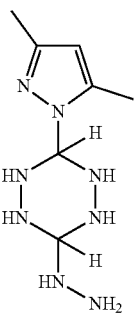

3-(3,5-dimethyl-1H-pyrazol-1-yl)-6-hydrazineyl-1,2,3,4,5,6-hexahydro-1,2,4,5-tetrazine (59)

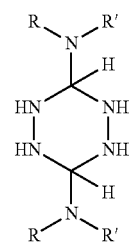

N3,N6-dialkyl-N3,N6-dialkyl'-1,2,3,4,5,6-hexahydro-1,2,4,5-tetrazine-3,6-diamine (60)

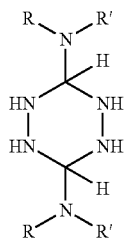

N3,N6-dialkyl-N3,N6-diaryl'-1,2,3,4,5,6-hexahydro-1,2,4,5-tetrazine-3,6-diamine

17. A method for inhibiting oxidation of an oxidizable material, comprising adding 3,6-bis(3,5-dimethyl-1H-pyrazol-1-yl)-1,4-dihydro-1,2,4,5-tetrazine to the oxidizable material, wherein the 3,6-bis(3,5-dimethyl-1H-pyrazol-1-yl)-1,4-dihydro-1,2,4,5-tetrazine is oxidized to consume an oxidizing species it is exposed to, thereby preventing the oxidizing species from oxidizing the oxidizable material.

18. The method of claim 17, wherein the hydrotetrazine compound is configured to change color when undergoing an oxidation reaction.

* * * * *